(12) United States Patent
Takatori et al.

(10) Patent No.: US 11,002,382 B2
(45) Date of Patent: May 11, 2021

(54) CABLE GUIDE AND DETECTION DEVICE WITH CABLE GUIDE

(71) Applicant: NIHON KOHDEN CORPORATION, Tokyo (JP)

(72) Inventors: Fumihiko Takatori, Tokorozawa (JP); Masayuki Inoue, Tokorozawa (JP)

(73) Assignee: NIHON KOHDEN CORPORATION, Tokyo (JP)

( * ) Notice: Subject to any disclaimer, the term of this patent is extended or adjusted under 35 U.S.C. 154(b) by 113 days.

(21) Appl. No.: 16/142,436

(22) Filed: Sep. 26, 2018

(65) Prior Publication Data

US 2019/0107229 A1 Apr. 11, 2019

(30) Foreign Application Priority Data

Oct. 6, 2017 (JP) ................ JP2017-196106

(51) Int. Cl.
| | |
|---|---|
| *F16L 3/12* | (2006.01) |
| *G01N 33/497* | (2006.01) |
| *H02G 3/00* | (2006.01) |
| *A61B 5/08* | (2006.01) |
| *A61B 5/083* | (2006.01) |

(52) U.S. Cl.
CPC ............ *F16L 3/1226* (2013.01); *A61B 5/082* (2013.01); *G01N 33/497* (2013.01); *H02G 3/00* (2013.01); *A61B 5/0836* (2013.01); *A61B 2562/221* (2013.01)

(58) Field of Classification Search
CPC .... H02G 3/00; A61B 5/082; A61B 2562/221; A61B 5/0836; G01N 33/497; F16L 3/1226; G02B 6/4292; G02B 6/4283; G02B 6/4274; G02B 6/4214; G02B 6/4201; G02B 6/4293; G02B 6/426; G02B 6/4281; G02B 6/3885
See application file for complete search history.

(56) References Cited

U.S. PATENT DOCUMENTS

| | | | | |
|---|---|---|---|---|
| 8,925,545 | B2 * | 1/2015 | Wondka | A61M 16/10 |
| | | | | 128/204.23 |
| 9,379,467 | B2 * | 6/2016 | Shimotsu | G02B 6/4284 |
| 2002/0108437 | A1 * | 8/2002 | Koch | A61B 5/0836 |
| | | | | 73/204.11 |
| 2009/0239420 | A1 * | 9/2009 | Nishio | G02B 6/4201 |
| | | | | 439/656 |
| 2015/0105639 | A1 | 4/2015 | Watanabe | |
| 2017/0028944 | A1 * | 2/2017 | Kimura | B60R 16/027 |

FOREIGN PATENT DOCUMENTS

JP 2015-073784 A 4/2015

* cited by examiner

*Primary Examiner* — Brandi N Hopkins
(74) *Attorney, Agent, or Firm* — Pearne & Gordon LLP (57) ABSTRACT

A cable guide is configured to be detachably attached to a detection device having a cable lead-out portion from which a cable extends in a predetermined direction. The cable guide includes a guide portion configured to change a lead-out direction of the cable with respect to the cable lead-out portion, and an attachment portion configured to attach the guide portion to the detection device.

20 Claims, 6 Drawing Sheets

CABLE GUIDE AND DETECTION DEVICE WITH CABLE GUIDE

CROSS-REFERENCE TO RELATED APPLICATION

The present application claims priority from Japanese Patent Application No. 2017-196106 filed on Oct. 6, 2017, the entire content of which is incorporated herein by reference.

BACKGROUND

The presently disclosed subject matter relates to a cable guide and a detection device with the cable guide, the cable guide configured to guide a direction of a cable led out from the detection device.

A long cable is used for a detection device configured to be attached to a body of a subject to detect physiological information. A related art cable guide is a shape retainer for holding this type of cable onto the subject (see, e.g., JP2015-073784A). The shape retainer has lower flexibility than the cable to which the shape retainer is attached. The shape retainer attached to the cable is deformed into a bent shape that fits for example an ear of the subject, and is attached to the subject to hold the cable onto the subject.

In accordance with recent downsizing of detection devices, there are increasing options as to a location of placing a detection device for detecting physiological information, and it is sometimes desired to change a cable lead-out direction from a cable lead-out portion of the detection device. The cable lead-out direction is a direction in which a cable is led out from the cable lead-out portion. The cable lead-out portion is a portion at which the detection device and the cable led out from the detection device are connected to each other.

However, the related art shape retainer is provided at a location distant from the cable lead-out portion. Therefore, even if the shape retainer is used in a bent and deformed manner, the cable lead-out direction with respect to the cable lead-out portion cannot be changed.

SUMMARY

The presently disclosed subject matter provides a cable guide and a detection device with cable guide capable of changing the cable lead-out direction with respect to the cable lead-out portion of the detection device.

According to an aspect of the presently disclosed subject matter, a cable guide is configured to be detachably attached to a detection device having a cable lead-out portion from which a cable extends in a predetermined direction. The cable guide includes a guide portion configured to change a lead-out direction of the cable with respect to the cable lead-out portion, and an attachment portion configured to attach the guide portion to the detection device.

According to another aspect of the presently disclosed subject matter, a detection device with cable guide includes the cable guide described above and the detection device to which the cable guide is detachably attachable.

According to another aspect of the presently disclosed subject matter, a detection device with cable guide includes the detection device having a housing, an attachment portion provided integrally with the housing, and a guide portion supported by the attachment portion, the guide portion being configured to change a lead-out direction of the cable.

DETAILED DESCRIPTION

Hereinafter, embodiments of the presently disclosed subject matter will be described with reference to the drawings. In the specification and drawings, the terms "up", "down", "left", "right", "front", and "rear" are used for convenience to indicate positional relationship between elements, and are not intended to limit the orientation in actual use.

First Embodiment

Figure 1:
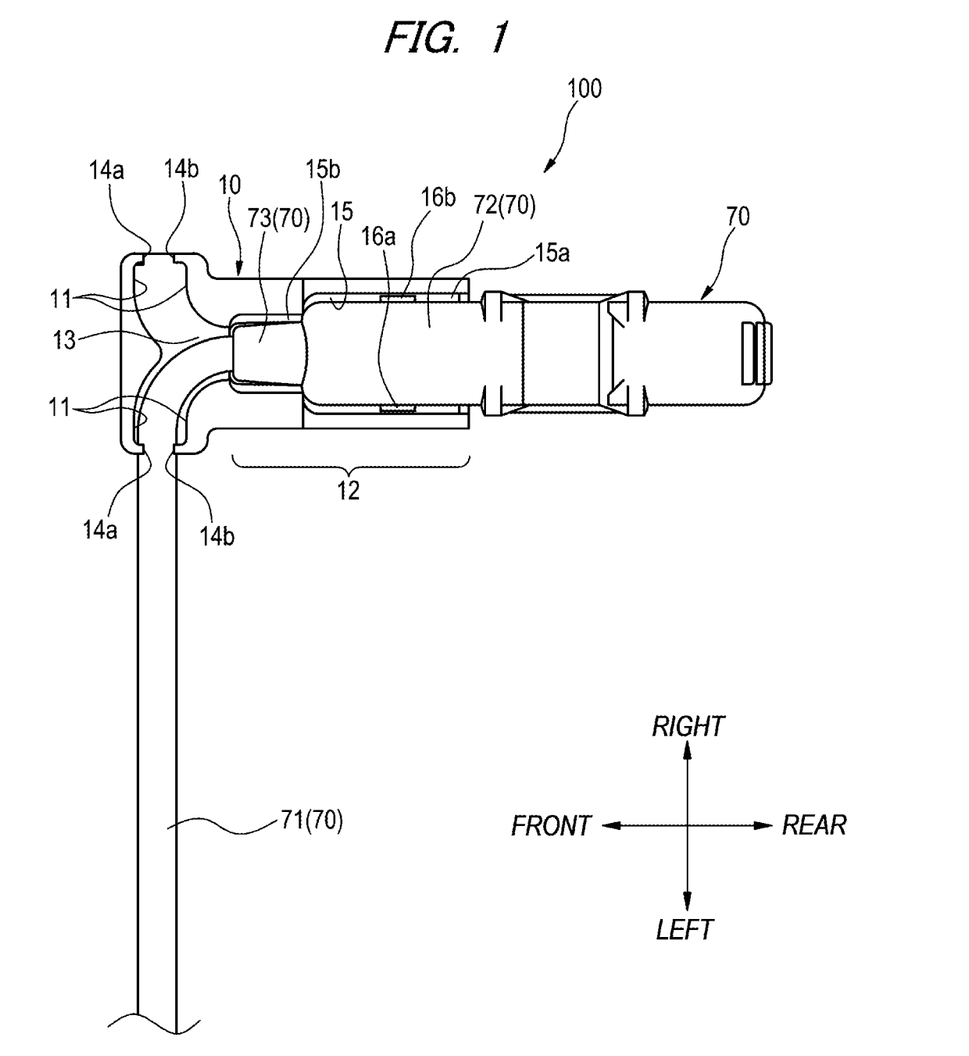
FIG. 1 is a top view of a detection device a cable guide according to a first embodiment of the presently disclosed subject matter.
Figure 2:
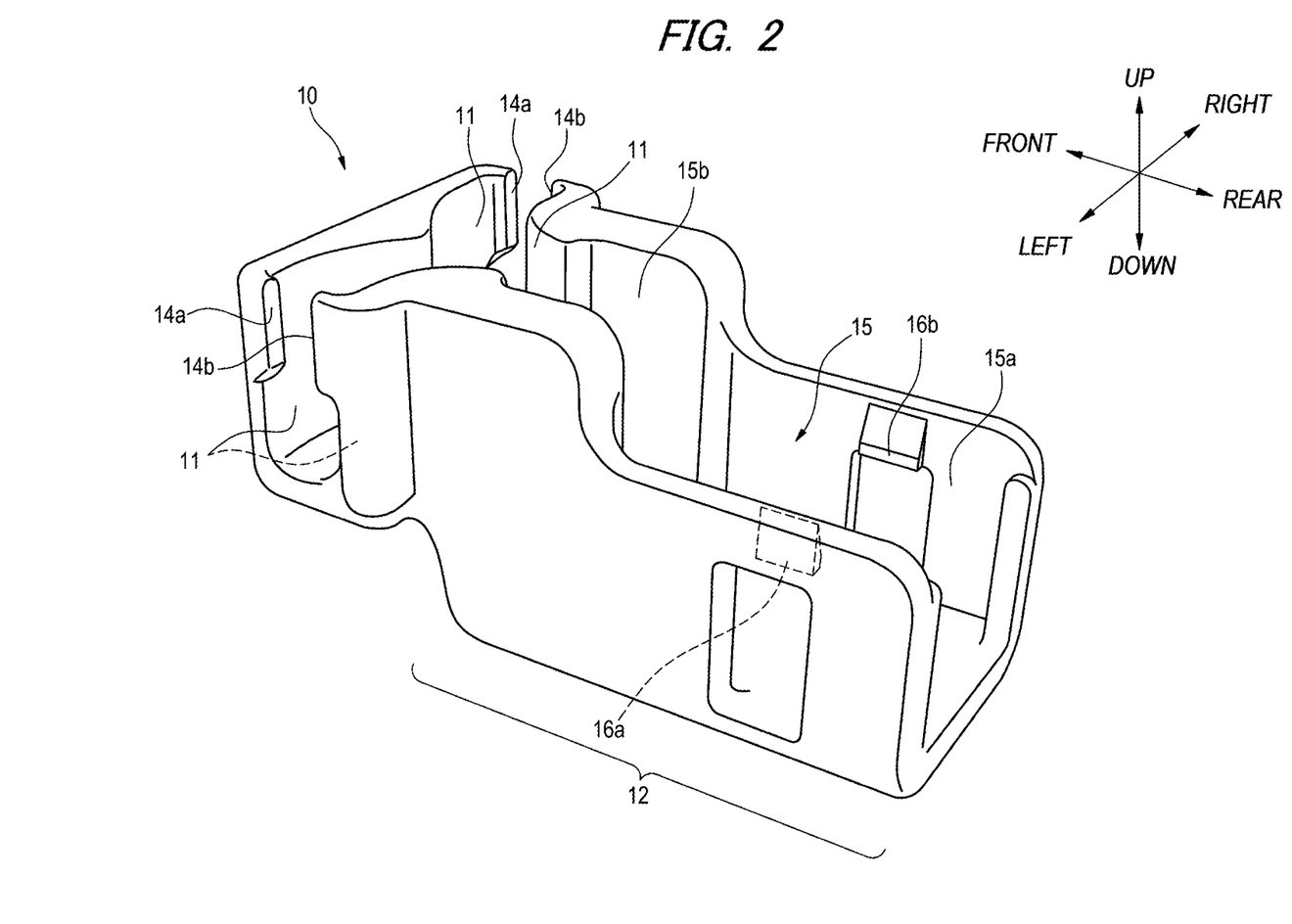
FIG. 2 is a perspective view of the cable guide of FIG. 1.
Figure 3:
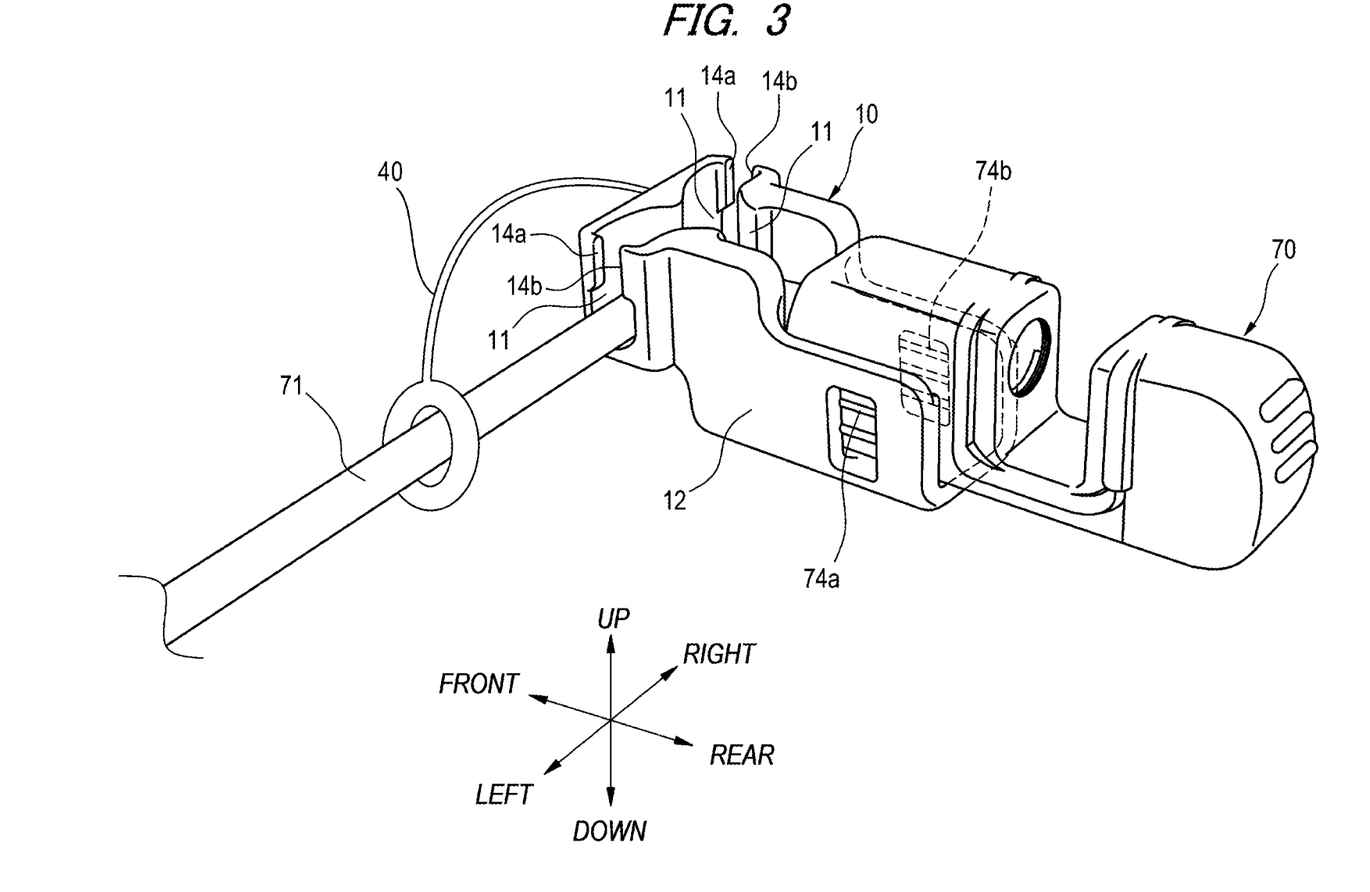
FIG. 3 is a perspective view of the detection device and the cable guide of FIG. 1.

A detection device and a cable guide according to a first embodiment of the presently disclosed subject matter will be described with reference to FIGS. 1 to 3. As shown in FIGS. 1 to 3, a detection device with cable guide 100 includes a cable guide 10 and a detection device 70. The cable guide 10 is detachably provided to the detection device 70.

The detection device 70 includes a main unit 72 and a lead-out portion 73 which a cable 71 is led out from the main unit 72. Examples of the detection device 70 include a respiratory gas detection device configured to optically measure the concentration of carbon dioxide contained in respiratory gas of a subject. For example, the main unit 72 has a light emitter and a light detector of a respiratory gas concentration sensor for measuring the concentration of carbon dioxide.

The cable 71 is provided to transmit signals detected by the main unit 72 to an external device. When the cable guide 10 is not attached to the detection device 70, the cable 71 extends straight forward (an example of a predetermined direction) from the lead-out portion 73. A cross-section of the cable 71 has a circular shape, an oval shape, an elliptical shape, a quadrangular shape or the like and includes flexible material. The lead-out portion 73 functions as a connection portion for connecting the main unit 72 and the cable 71 led out from the main unit 72 to each other.

The cable guide 10 includes a guide portion 11 configured to guide the lead-out direction of the cable 71 extending from the detection device 70 and an attachment portion 12 configured to attach the guide portion 11 to the detection device 70.

The guide portion 11 of the cable guide 10 is configured to change the lead-out direction of the cable 71 extending in a predetermined direction from the lead portion 73 of the detection device 70 with respect to the lead-out portion 73. The guide portion 11 has a pair of opposing side walls and is formed in a curved shape along which the lead-out direction is changed. The distance between the side walls of the guide portion 11 is slightly wider than a diameter or width of the cable 71. The guide portion 11 is configured to hold the cable 71 between the side walls and to guide the lead-out direction of the cable 71.

The guide portion 11 has a branching portion 13 configured such that the lead-out direction of the cable 71 extending forward from the lead-out portion 73 can be changed and led out in two directions, the left direction or the right direction. That is when the forward direction in which the cable 71 extends is set to 0 degrees, the lead-out direction can be changed in two directions of ±90 degrees.

The guide portion 11 has a pair of claw portions 14a, 14b opposing each other. In the illustrated example, the pair of claw portions 14a, 14b is provided at each outlet of the guide portion 11 through which the cable 71 extends out of the guide portion 11. The distance between the opposing claw portions 14a, 14b is slightly smaller than the diameter or the width of the cable 71. The pair of claw portions 14a, 14b is configured to guide the cable 71 such that the cable 71 is firmly held by the guide portion 11. The distance between the pair of claw portions 14a, 14b may be designed such that the cable 71 can be held between the claw portions 14a, 14b from both sides.

The attachment portion 12 of the cable guide 10 has a recess 15 into which the detection device 70 is fitted. The recess 15 includes a detection device holding portion 15a into which a front end portion of the main unit 72 is fitted and an lead-out portion holding portion 15b to which the lead-out portion 73 is fitted. The detection device holding portion 15a and the lead-out portion holding portion 15b are formed continuously in the front-rear direction of the cable guide 10, and the lead-out portion holding portion 15b is disposed on a side of the guide portion 11. The lead-out portion holding portion 15b is provided continuously to the branch portion 13 (see FIG. 1) that continues to the guide portion 11.

Inside the detection device holding portion 15a, a pair of locking portions 16a, 16b are provided in an opposing manner to hold the fitted main unit 72. The main unit 72 of the detection device 70 has convex portions 74a, 74b that engage with the locking portions 16a, 16b on both left-and right sides (see FIG. 3).

The guide portion 11 is attached to the detection device 70 via the attachment portion 12 by fitting a portion of the main unit 72 and the lead-out portion 73 into the recess 15 of the attachment portion 12. Further, the cable 71 extending from the lead portion 73 of the fitted detection device 70 is pressed into a space between the desired side walls of the guide portion 11, whereby the lead-out direction of the cable 71 is changed to a desired direction (either left or right in the illustrated example).

In the illustrated example, the cable guide 10 is attached to the detection device 70 from the lower side of the detection device 70. However, the cable guide 10 may be attached from the upper side of the detection device 70.

According to the detection device with cable guide 100 and the cable guide 10 configured as described above, by attaching the cable guide 10 to the detection device 70, it is possible to change the lead-out direction of the cable 71 extending to a predetermined direction (forward direction in the illustrated example) from the lead-out portion 73 of the detection device 70. For example, when the detection device 70 is to be used with the lead-out direction of the cable 71 being left or right, the cable guide 10 can be attached to the detection device 70 to change the lead-out direction of the cable 71 to either the left or the right. When the detection device 70 is desired to be used with the lead-out direction of the cable 71 being the forward direction, the cable guide 10 may be removed from the detection device 70.

The direction in which the guide portion 11 changes the lead-out direction is not limited to leftward and rightward directions. It may be changed to one or more of upward, downward, leftward, rightward, and any inclined directions.

The guide portion 11 has the pair of claw portions 14a, 14b, and the pair of claw portions 14a, 14b are formed at positions facing each other with a distance smaller than the diameter or the width of the cable 71. Therefore, the guide portion 11 can guide the cable 71 in a state where the cable 71 is firmly held by the cable guide 10. According to the pair of claw portions 14a, 14b formed at a distance capable of sandwiching the cable 71 from both sides, the cable 71 can be guided with the cable 71 being sandwiched between the claw portions 14a, 14b.

When the detection device 70 is used without the cable guide 10 and strong pulling force is applied unintentionally to the cable 71, the cable 71 may be bent at a steep angle (for example, a right angle) at the lead-out portion 73. In contrast, when the detection device 70 is used with the guide portion 11 is, the cable 71 is guided along the curved shape of the guide portion 11. Therefore, even when strong pulling force is applied to the cable 71, the cable 71 is prevented from being bent at a radius of curvature smaller than the radius of curvature of the guide portion 11, and it is possible to prevent the cable 71 from being bent at a steep angle.

The cable guide 10 may be configured to be attachable to different types of detection devices, in which case the cable lead-out direction can be changed for a plurality of types of detection devices using one cable guide 10.

The cable 71 of the detection device 70 and the cable guide 10 may be connected using a connector 40 such as a strap or a hook. For example, as shown in FIG. 3, the connector 40 may be a strap having one end formed in an annular shape so as to be slidably attachable to the outer periphery of the cable 71 and the other end fixed to the cable guide 10 (the guide portion 11 or the attachment portion 12). The connector 40 can prevent the cable guide 10 from becoming missing when being removed from the detection device 70.

Second Embodiment

Figure 4:
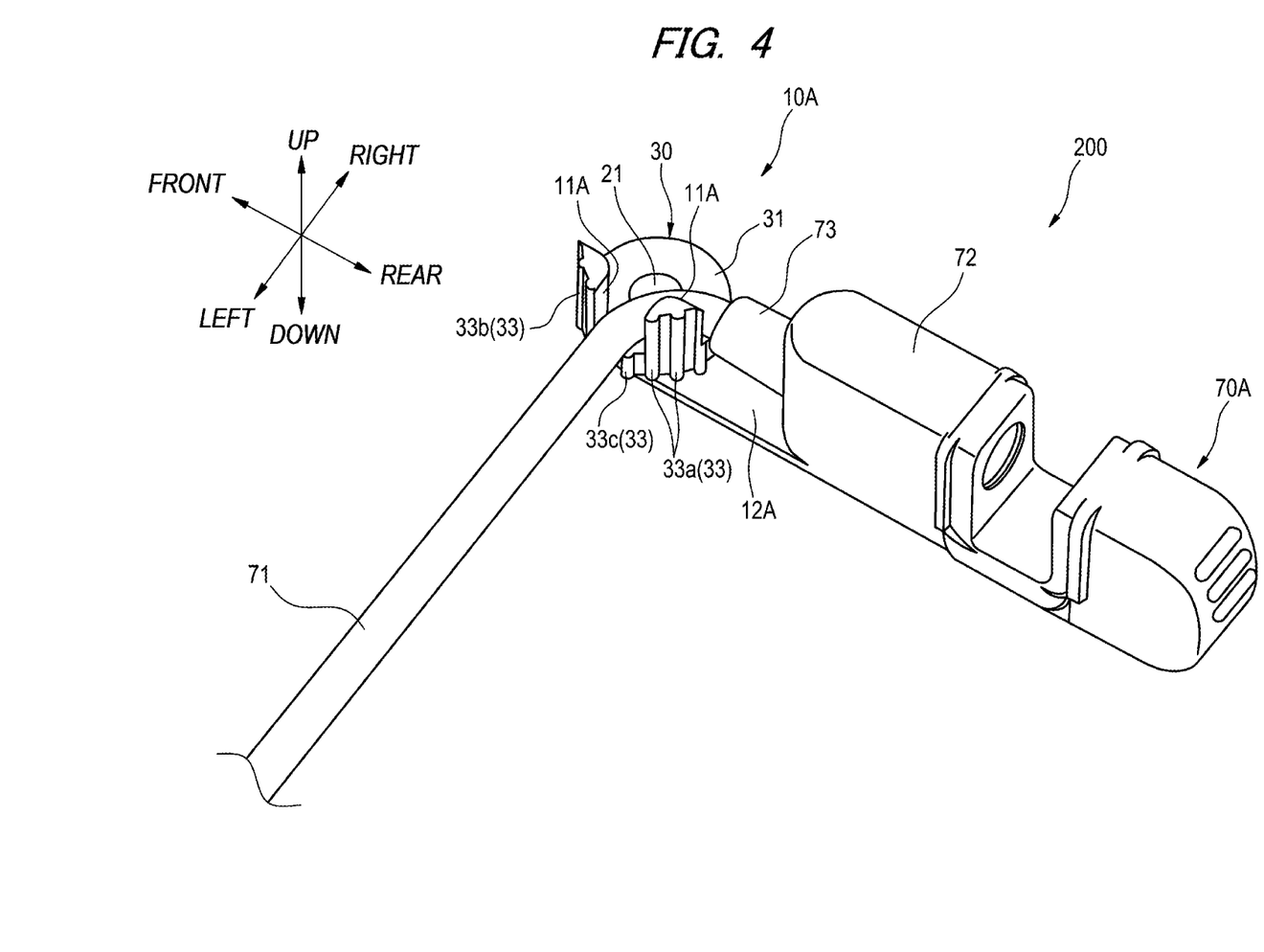
FIG. 4 is a perspective view of a detection device and a cable guide according to a second embodiment of the presently disclosed subject matter.
Figure 5:
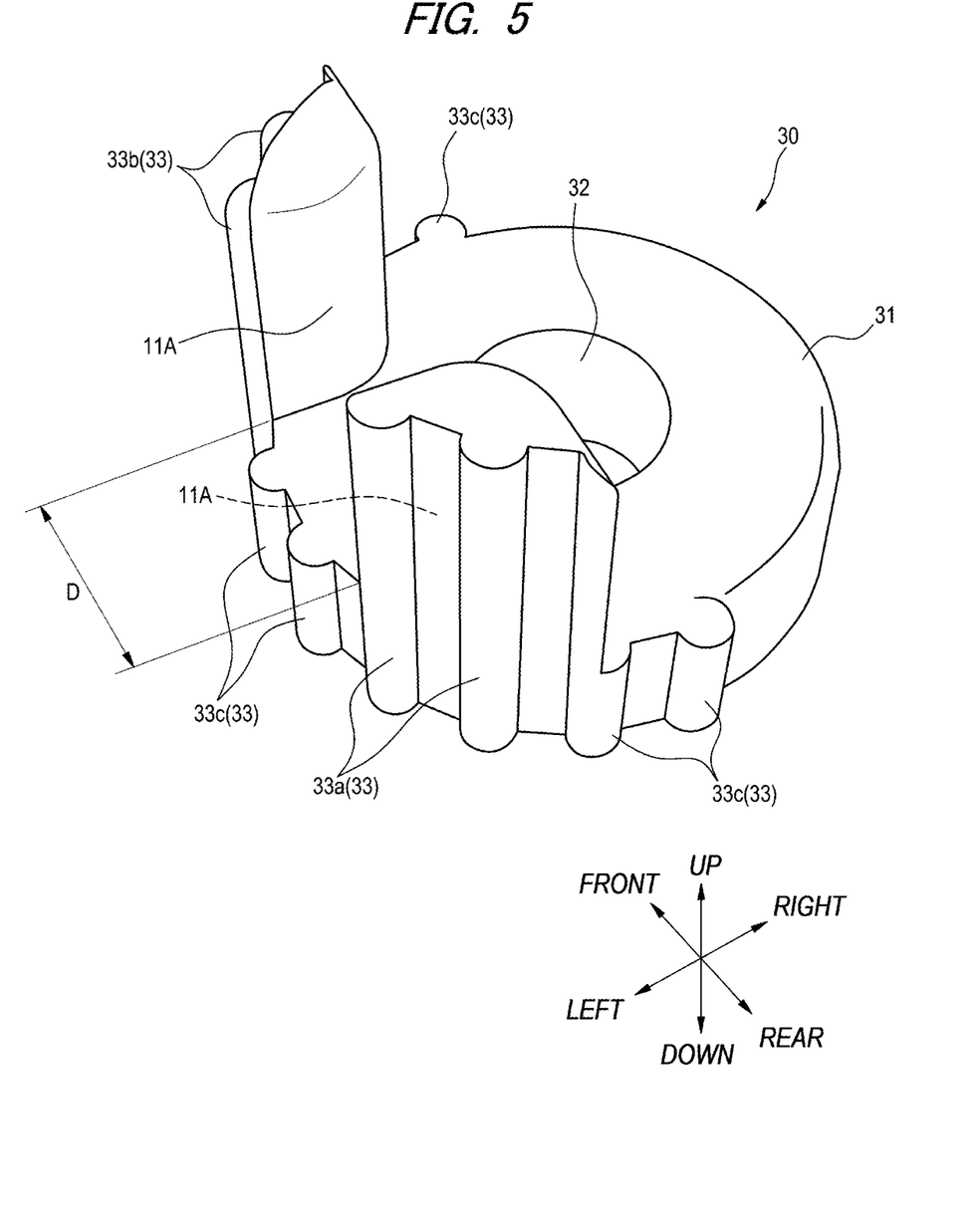
FIG. 5 is a perspective view of a rotary piece of the cable guide of FIG. 4.
Figure 6:
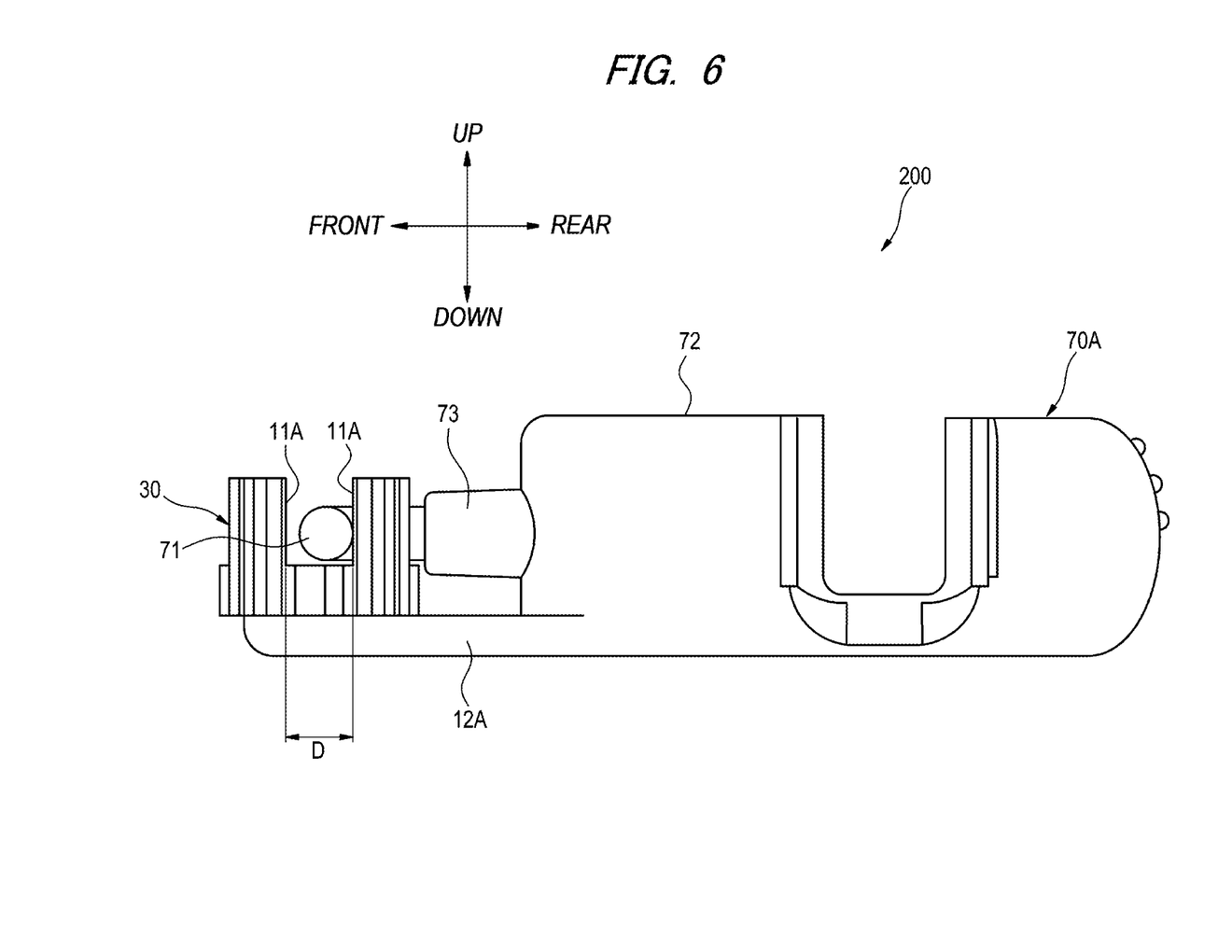
FIG. 6 is a left side view of the detection device and the cable guide of FIG. 4.

A detection device and a cable guide according to a second embodiment of the presently disclosed subject matter will be described with reference to FIGS. 4 to 6. The same or similar elements as those of the first embodiment are denoted by the same reference numerals, and description thereof will be omitted where appropriate. As shown in FIGS. 4 to 6, the detection device with cable guide 200 includes a cable guide 10A and a detection device 70A.

The cable guide 10A includes an attachment portion 12A integrally provided on the main unit 72 (an example of a housing) of the detection device 70A and a guide portion 11A that is rotatable with respect to the attachment portion 12A. The detection device 70A differs from the detection device 70 of the first embodiment in that the attachment portion 12A is integrally provided, but other configurations and functions are the same or similar as those of the detection device 70.

The attachment portion 12A is provided at a lower end portion of the detection device 70A so as to extend forward from the detection device 70A along the longitudinal direction (front-rear direction) of the detection device 70A. The attachment portion 12A is provided below the lead portion 73 of the detection device 70 A so as to face the lead-out portion 73 and extends forward. In the illustrated example, the attachment portion 12A is formed in a plate shape having the same width as the width of the detection device 70A in the left-right direction. A cylindrical shaft 21 supporting a rotary piece 30 is provided upright on the upper surface of the distal end portion of the attachment portion 12A.

The rotary piece 30 includes a disk portion 31, a hole 32 formed at a central portion of the disk portion 31, a guide portion 11A formed at the vicinity of the peripheral edge of the disk portion 31, and protrusions 33 formed on an outer peripheral portion of the disk portion 31.

The shaft 21 of the attachment portion 12A is inserted into the hole 32. The rotary piece 30 is supported by the attachment portion 12A and is configured to be rotatable with respect to the attachment portion 12A with the shaft 21 as a rotation axis.

The guide portion 11A is configured as guide walls provided upright on the disk portion 31. The cable 71 extending from the lead-out portion 73 of the detection device 70A is arranged so as to pass through the guide portion 11A. A distance D between the guide walls of the guide portion 11A is slightly larger than the diameter or the width of the cable 71. An inner surface of the guide wall (a surface on a side of the hole 32) is formed in curved shape along which the cable 71 is led out.

The protrusions 33 include first protrusions 33a, second protrusions 33b, and small protrusions 33c. The first protrusions 33a and the second protrusions 33b are formed in the vertical direction along the outer surface of the guide walls constituting the guide portion 11A. In the illustrated example, two first protrusions 33a and two second protrusions 33b are formed. However, the number of protrusions 33 is not limited, and may be only one. The small protrusions 33c are formed in the vertical direction along the outer peripheral surface of the disk portion 31. The length of the first protrusions 33a and the second protrusions 33b is longer than the length of the small protrusions 33c. The first protrusions 33a, the second protrusions 33b, and the small protrusions 33c are formed at a protruding height that can catch a finger e.g., a nail of an operator (e.g., an inspection staff who performs measurement using the detection device 70A).

The guide portion 11A may be configured to be rotatable at least 180 degrees with respect to the attachment portion 12A. For example, the guide portion 11A is configured to be rotatable in a range of ±90 degrees, with the direction in which the attachment portion 12A extends, that is, the direction in which the lead-out portion 73 of the detection device 70A extends forward being 0°. The rotary piece 30 may be provided with an angle switching mechanism (not shown) so that the rotation angle can be changed by switching the rotation angle every predetermined angle (e.g., every 15 degrees).

The cable 71 extending from the lead-out portion 73 of the detection device 70A is arranged to pass through the guide portion 11A. In this state, the lead-out direction of the cable 71 is changed to a desired direction with respect to the lead-out portion 73 by holding the rotary piece 30 at the first protrusions 33a and the second protrusions 33b and rotating the rotary piece 30 with two fingers. The rotary piece 30 may be rotated by pushing small protrusions 33 with one finger.

According to the detection device with cable guide 200 and the cable guide 10A configured as described above, since the guide portion 11A is configured to be rotatable with respect to the attachment portion 12A of the detection device 70A, the lead-out direction of the cable 71 can be changed to a desired direction.

Further, since at least one protrusion 33 (33a, 33b, 33c) is formed on the outer peripheral portion of the rotary piece 30, the lead-out direction of the cable 71 can be easily changed to a desired angle.

Further, since the guide portion 11A is configured to be rotatable 180 degrees with respect to the attachment portion 12A, the lead-out direction of the cable 71 can be changed, for example, at any angle in the range of ±90 degrees, with the direction in which the lead-out portion 73 extends being 0 degrees.

In the example illustrated in FIG. 4, the shaft 21 is provided to extend in the vertical direction, and the rotary piece 30 is configured to rotate on a horizontal plane, but the rotation structure of the rotary piece 30 is not limited thereto. For example, the shaft 21 may be provided on the attachment portion 12A to extend in the front-rear direction, and the rotary piece 30 may be rotated on a plane perpendicular to the front-rear direction (i.e., the plane including the vertical direction and the left-right direction). Alternatively, the shaft 21 may be provided on the attachment portion 12A to extend in the left-right direction, and the rotary piece 30 may be rotated on a plane perpendicular to the left-right direction (i.e., the plane including the vertical direction).

In the illustrated example, the attachment portion 12A is integrally provided with the detection device 70A, but the presently disclosed subject matter is not limited thereto. For example, similarly to the cable guide 10 of the first embodiment, the attachment portion 12A may be configured as a separate piece from the detection device 70A and may include a recess to which the detection device is fitted, and the cable guide 10A having the rotatable guide portion 11A may be detachably attached to the detection device 70. That is, the cable guide 10A may be configured to be detachably attached to the detection device 70, and may have a guide portion 11A capable of changing the lead-out direction of the cable 71 by being rotated, and the attachment portion 12A via which the guide portion 11A can be attached to the detection device 70.

The presently disclosed subject matter is not limited to the embodiments described above, and it will be understood by a person skilled in the art that various changes and modifications can be made therein. For example, the material, shape, size, numerical value, form, number, arrangement location and the like of each element in the embodiments described above are optional and not limited as long as the presently disclosed subject matter can be achieved.

What is claimed is:

1. A cable guide configured to be detachably attached to a detection device having a cable lead-out portion from which a cable extends in a predetermined direction, the cable guide comprising;
    a guide portion configured to change a lead-out direction of the cable with respect to the cable lead-out portion; and
    an attachment portion configured to attach the guide portion to the detection device.

2. The cable guide according to claim 1, wherein the guide portion comprises a pair of claw portions, and
    wherein the pair of claw portions are provided at locations opposing each other with a distance smaller than a diameter of the cable or a width of the cable.

3. The cable guide according to claim 1, wherein the guide portion is configured to be rotatable with respect to the attachment portion.

4. The cable guide according to claim 1, wherein guide portion is provided as part of a rotary piece configured to be rotatable with respect to the attachment portion, and
    wherein the rotary piece comprises at least one protrusion.

5. The cable guide according to claim 3, wherein the cable guide is configured to be rotatable with respect to the attachment portion in a range of at least 180 degrees.

6. The cable guide according to claim 1, further comprising a connector configured to connect the cable and the cable guide to each other.

7. The cable guide according to claim 1, wherein the guide portion has a pair of opposing side walls that are formed in a curved shape along which the lead-out direction is changed.

8. The cable guide according to claim 1, wherein the guide portion is configured to change the lead-out direction of the cable from the predetermined direction to a desired direction, wherein the desired direction is ±90 degrees from the predetermined direction.

9. The cable guide according to claim 1, wherein:
   the guide portion defines a curved channel having a first end and a second end, and
   the curved channel is configured to receive the cable such that the cable extends through the first end along the lead-out direction and extends through the second end along a desired direction that is different from the predetermined direction.

10. The cable guide according to claim 9, wherein the desired direction is ±90 degrees from the predetermined direction.

11. A detection device and cable guide,
   the detection device comprising a cable lead-out portion and a cable extending from the cable lead-out portion in a predetermined direction, and
   the cable guide comprising:
      a guide portion configured to change a lead-out direction of the cable with respect to the cable lead-out portion; and
      an attachment portion configured to detachably attach the guide portion to the detection device.

12. The detection device and cable guide according to claim 11, wherein the detection device includes a respiratory gas detection device.

13. The detection device and cable guide according to claim 11, wherein the guide portion has a pair of opposing side walls that are formed in a curved shape along which the lead-out direction is changed.

14. The detection device and cable guide according to claim 11, wherein:
   the guide portion defines a curved channel having a first end and a second end, and
   the curved channel is configured to receive the cable such that the cable extends through the first end along the lead-out direction and extends through the second end along a desired direction that is different from the predetermined direction.

15. The detection device and cable guide according to claim 14, wherein the desired direction is ±90 degrees from the predetermined direction.

16. A detection device and cable guide,
   the detection device comprising a housing, a cable lead-out portion connected to the housing, and a cable connected to the cable lead-out portion and extending from the cable lead-out portion in a predetermined direction; and
   the cable guide comprising:
      an attachment portion provided integrally with the housing, and
      a guide portion supported by the attachment portion, the guide portion being configured to change a lead-out direction of the cable.

17. The detection device and cable guide according to claim 16, wherein the detection device includes a respiratory gas detection device.

18. The detection device and cable guide according to claim 16, wherein the guide portion has a pair of opposing side walls that are formed in a curved shape along which the lead-out direction is changed.

19. The detection device and cable guide according to claim 16, wherein:
   the guide portion defines a curved channel having a first end and a second end, and
   the cable extends through the curved channel such that the cable extends through the first end along the lead-out direction and extends through the second end along a desired direction that is different from the predetermined direction.

20. The detection device and cable guide according to claim 19, wherein the desired direction is ±90 degrees from the predetermined direction.

* * * * *